United States Patent [19]

Pitt et al.

[11] Patent Number: 5,763,150
[45] Date of Patent: Jun. 9, 1998

[54] SURFACTANTS AND HYDROPHILIC COLLOID COMPOSITIONS AND MATERIALS CONTAINING THEM

[75] Inventors: Alan Robert Pitt, Sandridge; Trevor John Wear, South Harrow; Danuta Gibson, Garston, all of England

[73] Assignee: Eastman Kodak Company, Rochester, N.Y.

[21] Appl. No.: 685,082

[22] Filed: Jul. 23, 1996

[30] Foreign Application Priority Data

Jul. 25, 1995 [GB] United Kingdom ............... 9515204

[51] Int. Cl.$^6$ .................. G03C 1/38; G03C 7/388; C07C 143/67; C07C 149/20
[52] U.S. Cl. ............... 430/546; 430/449; 430/634; 252/312; 252/354; 560/14; 560/151
[58] Field of Search .............. 430/546, 634, 430/449; 252/354, 312; 560/14, 151

[56] References Cited

U.S. PATENT DOCUMENTS

| | | | |
|---|---|---|---|
| 2,785,134 | 3/1957 | Mathews et al. | 252/161 |
| 2,785,135 | 3/1957 | Mathews et al. | 252/161 |
| 2,949,360 | 8/1960 | Julian | 430/546 |
| 3,755,217 | 8/1973 | Schrader | 260/2.5 L |
| 3,948,663 | 4/1976 | Shiba et al. | 430/505 |
| 4,058,543 | 11/1977 | Mack | 260/45.75 S |
| 4,347,308 | 8/1982 | Takeuchi et al. | 430/529 |
| 4,988,610 | 1/1991 | Pitt et al. | 430/449 |
| 5,135,844 | 8/1992 | Bagchi et al. | 430/546 |
| 5,380,628 | 1/1995 | Sawyer et al. | 430/449 |
| 5,484,695 | 1/1996 | Pitt et al. | 430/546 |
| 5,543,555 | 8/1996 | Pitt et al. | 430/546 |
| 5,565,309 | 10/1996 | Bagchi et al. | 430/546 |

FOREIGN PATENT DOCUMENTS

| | | |
|---|---|---|
| 560457 | 9/1993 | European Pat. Off. |
| 591861 | 4/1994 | European Pat. Off. |
| 674221 A1 | 9/1995 | European Pat. Off. |
| 56/019042 | 2/1981 | Japan |
| 56/114944 | 9/1981 | Japan |
| 56/114945 | 9/1981 | Japan |
| 93/03420 | 2/1993 | WIPO |

OTHER PUBLICATIONS

Research Disclosure, Dec. 1989; vol. 308; No. 119; pp. 993–1015.

*Primary Examiner*—Richard L. Schilling
*Attorney, Agent, or Firm*—Andrew J. Anderson

[57] ABSTRACT

Surfactants useful as dispersing aids in the preparation of compositions comprising a hydrophilic colloid having hydrophobic particles dispersed therein have the structure

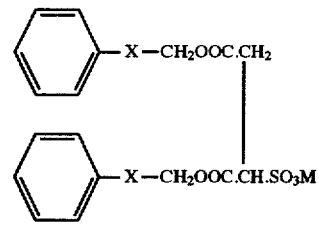

I wherein
M is a cation;
X represents a group having the structure

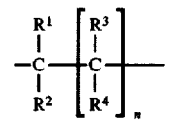

wherein
each of $R^1$, $R^2$, $R^3$ and $R^4$ independently represents hydrogen or alkyl; or $R^1$ and $R^2$ taken together represent cycloalkyl; or $R^3$ and $R^4$ taken together represent cycloalkyl; and,
n represents 0 or 1;
provided that the total number of carbon atoms in each X group is 3 or 4, and when $R^1$ is hydrogen $R^2$ is other than methyl. Such surfactants offer coating and photographic property advantages when incorporated in multilayer photographic materials comprising a support bearing a plurality of hydrophilic colloid layers.

8 Claims, No Drawings

SURFACTANTS AND HYDROPHILIC COLLOID COMPOSITIONS AND MATERIALS CONTAINING THEM

FIELD OF THE INVENTION

The invention relates to surfactants and their use as dispersing aids in the preparation of hydrophilic colloid compositions having hydrophobic particles dispersed therein. Such compositions may be used in the preparation of multilayer photographic materials.

BACKGROUND OF THE INVENTION

A wide variety of surfactants have been described for use in the preparation of photographic materials.

JP56-19042 describes various diester sulfoitaconates as dispersing aids for photographic additives. The two ester linked hydrophobic groups include a number of substituted or unsubstituted alkyl or aryl groups.

U.S. Pat. No. 3,948,663 describes photographic materials containing certain sulfosuccinate surface active agents and refers to their possible use as dispersing aids and coating aids. A specific example of such a surface active agent is sodium dioctyl sulfosuccinate which is commercially available as Aerosol™OT.

WO93/03420 describes a method of making fine particle photographic coupler dispersions which comprises forming a dispersion of photographic coupler, coupler solvent and auxiliary coupler solvent in an aqueous gelatin medium containing at least about 1% by weight of an anionic surfactant having a hydrophobicity of 2–10 log P(OH) and washing the dispersion with water for a time sufficient to remove at least one fourth of the surfactant. Anionic surfactants of diverse structures may be employed and included among several named surfactants is diphenylbutyl sodium sulfosuccinate.

A shortcoming of the use of surfactants described in JP56-19042 and U.S. Pat. No. 3,948,663 is the very low surface tension values exhibited by the compounds at concentrations above their critical micelle concentration (CMC). In the simultaneous multilayer coating of hydrophilic colloid layers, it is essential that the surface tension of the top layer is lower than that of any of the underlying layers if it is to remain spread during the coating operation. If one of the underlying layers has a lower surface tension than the top layer it drives the top layer in from the edges towards the centre of the coating. This is often termed "edge retraction". The larger the surface tension imbalance, the more disruptive is the effect. Large differences can cause retraction of the whole coating pack and general layer inversions. The surface tension of underlying layers in the multilayer coating of photographic materials is often dominated by the surfactant dispersing aid that is used to stabilize the emulsified hydrophobic particles therein e.g. colour couplers and their associated solvents.

When such prior art surfactants are used as dispersing aids for emulsified materials that are incorporated in underlying hydrophilic colloid layers during simultaneous multilayer coating, a constraint is put on the choice of surfactant or surfactant concentration required for the overlying layers i.e. coating latitude is relatively narrow.

Another shortcoming of the use of the surfactants described in JP56-19042 and U.S. Pat. No. 3,948,663 as dispersing aids for photographic couplers in hydrophilic colloid compositions is that the photographic properties of such compositions e.g. the liquid dispersion reactivity, can be less than desired.

PROBLEM TO BE SOLVED BY THE INVENTION

The invention overcomes the coating latitude problem associated with some of the prior art dipersing aids.

Limitations in the photographic properties of dispersions of photographic couplers in hydrophilic colloids can be overcome.

SUMMARY OF THE INVENTION

The invention provides compounds having the structure

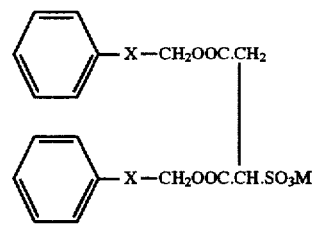

I wherein

M is a cation;

X represents a group having the structure

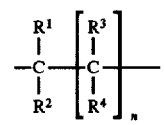

wherein each of $R^1$, $R^2$, $R^3$ and $R^4$ independently represents hydrogen or alkyl; or $R^1$ and $R^2$ taken together represent cycloalkyl; or $R^3$ and $R^4$ taken together represent cycloalkyl; and, n represents 0 or 1;

provided that the total number of carbon atoms in each X group is 3 or 4, and when $R^1$ is hydrogen $R^2$ is other than methyl.

The invention also provides a composition comprising a hydrophilic colloid having hydrophobic particles dispersed therein with the aid of a surfactant having the structure I.

A multilayer photographic material comprises a support bearing a plurality of hydrophilic colloid layers including at least one light-sensitive silver halide emulsion layer wherein at least one of the underlying layers of the material contains hydrophobic particles dispersed therein with the aid of a surfactant having the structure I.

A method of preparing a multilayer photographic material comprises (a) simultaneously coating on a support a plurality of aqueous hydrophilic colloid layers including at least one light-sensitive-silver halide emulsion layer wherein at least one of the underlying layers contains hydrophobic particles dispersed therein with the aid of a surfactant having the structure I, and (b) drying the coated layers.

ADVANTAGEOUS EFFECT OF THE INVENTION

By providing aqueous hydrophilic colloid melts with high surface tension minima, the invention enables increased coating latitude.

Improved photographic performance can be achieved with dispersions of a photographic coupler in a hydrophilic colloid. The nature of the improvement depends on the type of coupler dispersion. For example, with a microprecipitated dispersion, the benefits include increased liquid dispersion reactivity. With a homogenized dispersion, the benefits include increased contrast in coated product.

DETAILED DESCRIPTION OF THE INVENTION

In structure I, the cation M is a positively charged atom or group of atoms preferably chosen from alkali metal cations e.g. $Na^+$; ammonium or tetraalkylammonium.

$R^1$, $R^2$, $R^3$ and $R^4$ may be selected from the group consisting of methyl, ethyl and propyl; $R^1$ and $R^2$ taken together or $R^3$ and $R^4$ taken together may be selected from the group consisting of cyclopropylene and cyclobutylene; provided that the total number of carbon atoms in each X group is 3 or 4, and when $R^1$ is hydrogen $R^2$ is other than methyl.

Preferred compounds include those wherein $R^1$ and $R^2$ are each independently alkyl, or $R^3$ and $R^4$ are each independently alkyl.

A particularly preferred compound is represented by structure I wherein n is 1, $R^1$ and $R^2$ each represent hydrogen and $R^3$ and $R^4$ each represent methyl.

The compounds may-be water soluble or water dispersible.

The compounds may be prepared by the esterification of maleic acid with an appropriate phenylalkanol. A specific method which can be used in respect of all the compounds is given below in Example 1.

Compositions comprising a hydrophilic colloid having hydrophobic particles dispersed therein may be formed by a process comprising dispersing a hydrophobic material into an aqueous solution of a hydrophilic colloid in the presence of the surface active agent.

For homogenized dispersions, the surface active agent is used preferably in an amount from 0.4 to 2.0, more preferably from 0.6 to 0.9 weight percent based on the weight of the aqueous dispersion.

For microprecipitated dispersions, the surface active agent is used preferably in an amount that provides a molar ratio of surface active agent: hydrophobic material e.g. photographic coupler which is from 1:4 to 2:1.

Regardless of the particular method of preparation, dispersions can be made in accordance with the invention which avoid the coating latitude problems associated with the prior art by using less than about 1 weight percent of the surfactant and without requiring a washing step to remove at least one fourth of the surfactant.

The invention is particularly useful in the preparation of photographic compositions and materials;

In the following discussion of suitable materials for use in the compositions and materials of this invention, reference will be made to *Research Disclosure*, December, 1989, Item 308119, published by Kenneth Mason Publications, Ltd., Dudley Annex, 12a North Street, Emsworth, Hampshire, PO10 7DQ, UK. This publication will be identified hereafter by the term *Research Disclosure*.

A number of hydrophobic photographic additives used in light sensitive photographic materials are oil-soluble and are used by dissolving them in a substantially water-insoluble, high boiling point solvent which is then dispersed in an aqueous hydrophilic colloid solution with the assistance of a dispersing aid. Such oil-soluble additives include image forming dye couplers, dye stabilizers, antioxidants and ultraviolet radiation absorbing agents. A typical solvent used to dissolve the additive is aromatic e.g. di-n-butyl phthalate.

Gelatin is the preferred hydrophilic colloid, but other hydrophilic colloids can be used alone or in combination with gelatin.

Suitable methods of preparing photographic dispersions are described in *Research Disclosure*, Sections XIV A and XIV B. For example, homogenised oil in aqueous gelatin dispersions of photographic couplers can be prepared by dissolving the coupler in a coupler solvent and mechanically dispersing the resulting solution in an aqueous gelatin solution (see U.S. Pat. No. 2,322,027).

Alternatively, microprecipitated dispersions of photographic couplers prepared by solvent and/or pH shift techniques are becoming more widely used (see references: U.K. Patent No. 1,193,349; Research Disclosure 16468, December 1977 pp 75–80; U.S. Pat. No. 4,957,857 by K. Chari; U.S. Pat. Nos. 4,970,139 & 5,089,380 by P. Bagchi; U.S. Pat. No. 5,008,179 by K. Chari, W. A. Bowman & B. Thomas; U.S. Pat. No. 5,104,776 by P. Bagchi & S. J. Sargeant) and offer benefits in decreased droplet size and often increased reactivity relative to conventional oil-in-water homogenised dispersions.

Multilayer photographic materials according to the invention comprise one or more underlying layers formed from such compositions.

Preferred multilayer photographic materials include color materials of the type described in *Research Disclosure*, Sections VII A to VII K.

Methods of preparing multilayer photographic materials by simultaneously coating the layers are known. Particular methods are described in *Research Disclosure*, Sections XV A and XV B. Such methods include extrusion coating and curtain coating.

The hydrophobic material dispersed in the hydrophilic colloid may be a photographic coupler.

Couplers which form cyan dyes upon reaction with oxidized color-developing agents are described in such representative patents and publications as U.S. Pat. Nos. 2,772,162; 2,895,826; 3,002,836; 3,034,892; 2,747,293; 2,423,730; 2,367,531; 3,041,236; and 4,333,999; and Research Disclosure, Section VII D.

Couplers which form magenta dyes upon reaction with oxidized color developing agents are described in such representative patents and publications as: U.S. Pat. Nos. 2,600,788; 2,369,489; 2,343,703; 2,311,082; 3,152,896; 3,519,429; 3,062,653; and 2,908,573; and *Research Disclosure*, Section VII D.

Couplers which form yellow dyes upon reaction with oxidized and color developing agents are described in such representative patents and publications as: U.S. Pat. Nos. 2,875,057; 2,407,210; 3,265,506, 2,298,443; 3,048,194; and 3,447,928; and *Research Disclosures*, Section VII D.

Couplers which form colorless products upon reaction with oxidized color developing agents are described in such representative patents as: UK Patent No. 861,138; U.S. Pat. Nos. 3,632,345; 3,928,041; 3,958,993; and 3,961,959.

The couplers can be dissolved in a solvent and then dispersed in a hydrophilic colloid. Examples of solvents usable for this process include organic solvents having a high boiling point, such as alkyl esters of phthalic acid (for example, dibutyl phthalate, dioctyl phthalate, and the like), phosphoric acid esters (for example, diphenyl phosphate, triphenyl phosphate, tricresyl phosphate, dioctyl butyl phosphate, and the like) citric acid esters (for example, tributyl acetyl citrate, and the like) benzoic acid esters (for example, octyl benzoate, and the like), alkylamides (for example, diethyl laurylamides, and the like), esters of fatty acids (for example dibutoxyethyl succinate, dioctyl azelate, and the like), trimesic acid esters (for example, tributyl trimesate, and the like), or the like; and organic solvents having a boiling point of from about 30° to about 150° C., such as lower alkyl acetates (for example, ethyl acetate, butyl acetate, and the like), ethyl propionate, secondary butyl alcohol, methyl isobutyl ketone, b-ethoxyethyl acetate, methyl cellosolve acetate, or the like. Mixtures of organic solvents having a high boiling point and organic solvents having a low boiling point can also be used.

As the binder or the protective colloid for the photographic emulsion layers or intermediate layers of the photographic light-sensitive material of the present invention, gelatin is advantageously used, but other hydrophilic colloids can be used alone or together with gelatin.

As gelatin in the present invention, not only lime-processed gelatin, but also acid-processed gelatin may be employed. The methods for preparation of gelatin are described in greater detail in Ather Veis, *The Macromolecular Chemistry of Gelatin*, Academic Press (1964).

As the above-described hydrophilic colloids other than gelatin, it is possible to use proteins such as gelatin derivatives, graft polymers of gelatin and other polymers, albumin, casein, and the like; saccharides such as cellulose derivatives such as like, sodium alginate, starch derivatives, and the like; and various synthetic hydrophilic high molecular weight substances such as homopolymers or copolymers, for example, polyvinyl alcohol, polyvinyl alcohol semiacetal, poly-N-vinylpyrrolidone, polyacrylic acid, polymethacrylic acid, polyacrylamide, polyvinyl imidazole, polyvinylpyrazole, and the like.

In the photographic emulsion layers or other hydrophilic colloid layers of the photographic light-sensitive material of the present invention can be incorporated various surface active agents as coating aids or for other various purposes, for example, prevention of charging, improvement of slipping properties, acceleration of emulsification and dispersion, prevention of adhesion and improvement of photographic characteristics (for example, development acceleration, high contrast, and sensitization), and the like.

Surface active agents which can be used are nonionic surface active agents, for example, saponin (steroid-based), alkyene oxide derivatives (for example, polyethylene glycol, a polyethylene glycol/polypropylene glycol condensate, polyethylene glycol alkyl ethers or polyethylene glycol alkylaryl ethers, polyethylene glycol esters, polyethylene glycol sorbitan esters, polyalkylene glycol alkylamines or polyalkylene glycol alkylamides, and silicone/polyethylene oxide adducts, and the like), glycidol derivatives (for example, alkenylsuccinic acid polyglyceride and alkylphenol polyglyceride, and the like), fatty acid esters of polyhydric alcohols and alkyl esters of sugar, and the like; anionic surface active agents containing an acidic group, such as a carboxy group, a sulfo group, a phospho group, a sulfuric acid esters group, and a phosphoric acid ester group, for example, alkylcarboxylic acid salts, alkylsulfonic acid salts, alkylbenzenesulfonic acid salts, alkylnaphthalenesulfonic acid salts, alkylsulfuric acid esters, alkylphosphoric acid esters, N-acyl-N-alkyltaurines, sulfosuccinic acid esters, sulfoalkylpolyoxyethylene alkylphenyl ethers, and polyoxyethylene alkylphosphoric acid esters; amphoteric surface active agents, such as amino acids, aminoalkylsulfonic acids, aminoalkylsulfuric acid or aminoalkylphosphoric acid esters, alkylbetaines, and amine oxides; and cationic surface active agents, for example, alkylamine salts, aliphatic or aromatic quaternary ammonium salts, heterocyclic quaternary ammonium salts (for example, pyridinium and imidazolium) and aliphatic or heterocyclic phosphonium or sulfonium salts.

The surfactant dispersing aid of this invention may be used in conjunction with other surfactants, e.g. anionic and/or nonionic surfactants, which may be present for auxiliary purposes such as, additional dispersing aid, improved coating uniformity and/or rheology modification (e.g. reduced viscosity and shear thinning).

In the photographic emulsion layer of the photographic light-sensitive material used in the present invention, any of silver bromide, silver iodobromide, silver iodochlorobromide, silver chlorobromide and silver chloride may be used as the silver halide.

The light-sensitive silver halide contained in the photographic material can be processed following exposure to form a visible image by associating the silver halide with an aqueous alkaline medium in the presence of a developing agent contained in the medium or the material. Suitable types of photographic processing are described in *Research Disclosures*, Section XIX A to XIX J. Suitable developing agents are described in *Research Disclosures*, Section XX A to XX B.

The following Examples further illustrate the invention.

A number of compounds referred to in the Examples are as follows:

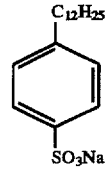

| Structure or Commercial Name or publication source | Chemical Name | Code (where used) |
|---|---|---|
| $C_{12}H_{25}.OSO_3.Na$ | Sodium dodecyl sulphate | SDS |
| $C_{12}H_{25}$ — ⌬ — $SO_3Na$ | Sodium dodecylbenzene sulphonate | SDBS |
| Aerosol ™ OT (Cyanamid) | Sodium di-2-ethylhexyl sulphosuccinate | AOT |
| $X = -(CH_2)_3-$ (structure I) | Sodium Di-4-phenylbutyl sulphosuccinate | $X = -(CH_2)_3-$ (structure I) |
| $X = -(CH_2)_2-$ (structure I) | Sodium Di-3-phenylpropyl sulphosuccinate | $X = -(CH_2)_2-$ (structure I) |

EXAMPLE 1

Synthesis of sodium di(2,2-dimethyl-3-phenylprop-1-yl)sulphosuccinate

A mixture of maleic acid (116.0 g, 1.00 mol), and 2,2-dimethyl-3-phenyl-1-propanol (328.5 g, 2.00 mol) and concentrated sulphuric acid (0.5 cm³) was suspended in toluene (260 cm³) and refluxed for 5 hours in a flask equipped with a Dean and Stark trap. On cooling, the toluene solution was diluted with ethyl acetate (800 ml) and washed with 1M sodium hydrogen carbonate (2×500 cm3). The organic layer was dried over magnesium sulphate and the solvent removed under reduced pressure (15 mm Hg, 50° C.) to give an intermediate diester as a clear oil (363.3 g, 89%).

A solution of sodium metabisulphite (104.5 g, 0.55 mol) in water (350 cm³) was added to a solution of this diester (204.2 g, 0.50 mol) in ethanol (350 cm³) and the mixture brought to reflux over 15 minutes. Sodium sulphite (56.7 g, 0.45 mol) was then added portionwise to the mixture over 30 minutes and the reaction refluxed for 5.5 hours. The reaction mixture was evaporated at reduced pressure (15 mm Hg, 22° C.) to remove ethanol and the resulting aqueous solution was then extracted into ethyl acetate (2×400 cm³). The organic solution was dried over anhydrous magnesium sulphate, filtered, evaporated at reduced pressure (15 mm Hg, 22° C.), and finally freeze dried to give the product as a white crystalline solid (203.2 g, 79%). Data from infra-red and 1H NMR spectroscopy was consistent with the proposed product, sodium di(2,2-dimethyl-3-phenylprop-1-yl) sulphosuccinate.

EXAMPLE 2

Surface Tension Measurements

Surface tension measurements were conducted in solutions containing 7% deionised Type IV bone gelatin in water at 40° C. to simulate a coating melt. Static surface tensions were measured as a function of surfactant concentration using the Wilhelmy technique.

The measurement of surface tension of an aqueous solution containing surfactant was measured over a concentration range including the critical micelle concentration using the Wilhelmy technique [Padday J F, 2nd Int. Congress of Surface Activity, I, 1, 1957] with a platinum blade.

Table 1A compares static surface tension data of a compound of the invention with comparison compounds.

TABLE 1A

Static Surface Tension (mN/m) of Solutions in 7% Deionised Type IV Bone Gelatin Water at 40° C.

| Compounds Tested | Wt % Concentration in 7% Deionised Gelatin solution | |
|---|---|---|
| X | 0.10% | 0.30% |
| Invention X = —CH$_2$C(CH$_3$)$_2$— | 36.7 | 36.3 |
| Comparison X = —(CH$_2$)$_3$— | 42.8 | 42.8 |
| Comparison AOT | 28.9 | 28.7 |

Comparative dynamic surface tension measurements were also determined by the same technique using an overflowing circular weir [ibid.]. The average surface age of the solutions in the overflowing weir has been estimated to be of the order of 0.1 seconds.

The particular conditions of use for the dynamic surface tension measurements were:

(i) Diameter of lip of circular weir, 37.5 mm;

(ii) No sintered glass disc;

(iii) Flow rate over weir, 9 ml/sec.

(iv) Temperature, 40° C. for aqueous gelatin solutions. Dynamic surface tensions (DST) of this order of surface age have been found to be more relevant to the process of coating multilayers of photographic elements than static/equilibrium values. Table 1B shows the corresponding DST data measured using the 'Weir' technique.

TABLE 1B

Dynamic Surface Tension (mN/m) of Solutions in 7% Deionised Type IV Bone Gelatin Water at 40° C. using the Weir Method

| Compounds Tested | Wt % Concentration in 7% Deionised Gelatin solution | |
|---|---|---|
| X | 0.10% | 0.30% |
| Invention X = —CH$_2$C(CH$_3$)$_2$— | 37.6 | 36.3 |
| Comparison X = —(CH$_2$)$_3$— | 43.7 | 42.8 |
| Comparison AOT | 30.1 | 29.2 |

At low concentrations DST values are higher than the corresponding static surface tension values. However, as is seen here, the DST values approach the limiting static values at fairly low concentration levels if surfactants possess a moderate balance of hydrophilic and lipophilic properties.

The di-ω-phenylalkyl sulphosuccinate of this invention gives much higher values of static and dynamic surface tension than corresponding dialkyl sulphosuccinates such as Aerosol OT. Hence the compounds of the current invention maintain the advantage over aliphatic sulphosuccinates of a higher limiting surface tension value, and as such can be expected to give a better coating latitude.

EXAMPLE 3

Increased dispersion reactivity with Microprecipitated Dispersions

Microprecipitated dispersions were made with the Coupler A shown below

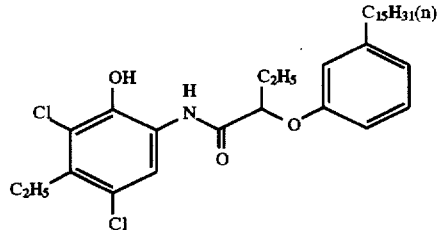

and various dispersing aids.

The Coupler A (20 g) was dissolved in a mixture of propan-1-ol (40 g) and 20% sodium hydroxide solution (5 g) at 60° C. and poured into a solution of surfactant (weight equimolar with coupler) and polyvinylpyrrolidone (10 g) in water (600 g). The resulting micellar solution was reduced to pH 6.0 by the dropwise addition of 15% propanoic acid, to form the crude microprecipitated dispersion which was then dialysed through Amicon hollow fibre ultrafiltration cartridges and concentrated to a fifth of its volume.

The liquid dispersion reactivity measurements were made according to the method described by Bagchi in U.S. Pat. Nos. 4,970,139; 5,089,380 and 5,104,776. Particle size was measured by photon correlation spectroscopy. The objective of the study was to compare the performance of the surfactant of the invention as a dispersing aid against other surfactants.

TABLE 2

Microprecipitated dispersions of Coupler A Physical data.

| SURFACTANT (dispersing aid) | Liquid Dispersion Reactivity | Mean Particle Diameter (nm) | Comment |
|---|---|---|---|
| X = —CH$_2$C(CH$_3$)$_2$— | 6597 | 152 | invention |
| X = —(CH$_2$)$_3$— | 5891 | 88 | comparison |
| AOT | 5188 | 192 | comparison |
| SDBS | 5386 | 219 | comparison |
| SDS | 4750 | 39 | comparison |

The above results show that the compound of this invention increases the liquid dispersion reactivity of the microprecipitated dispersion relative to other surfactants. In particular, the invention shows a significant advantage in reactivity over the similarly structured di-4-phenylbutyl sulphosuccinate (ratio of reactivities=1.12). As demonstrated here, the prior art compounds give higher reactivity than the aliphatic sulphosuccinate, AOT, and other conventional anionic surfactants.

Interestingly, the dispersion reactivity obtained in Table 2 is surfactant specific and does not correlate with the measured particle size.

EXAMPLE 4

Increased Contrast and Dmax with Homogenised Dispersions of Colour Coupler A Traditionally (see U.S. Pat No. 2,322,027 by Jelly and Vittum) colour couplers are dissolved in a high-boiling, water-insoluble solvent and mechanically dispersed in an aqueous gelatin solution containing surfactant to facilitate dispersion. Mean droplet sizes are usually significantly larger (typically, 0.2 μm) than those produced by microprecipitation techniques (typically, 0.02 μm).

The homogenised dispersions were made according to the following technique.

A dispersion was made of the following general formula:

| Coupler A | 11.7% |
|---|---|
| di-n-butylphthalate | 3.9% |
| gelatin | 9.5% |
| water & surfactant | 74.8% |

Coupler A was dissolved in di-n-butyl phthalate and heated at 140° C. until the coupler had completely dissolved. Gelatin was dissolved in water and heated to 70° C. Surfactant was added to the gelatin solution at a rate of 0.1 mole equivalent to coupler. The coupler solution was then added to the gelatin solution and homogenised for 3 minutes using a Kinematica Polytron set at 10,000 rpm and then passed (twice) through a Microfluidics Microfluidiser (model no. 110E) which was run at 10,000 psi pressure and a water bath temperature of 75° C.

A monochrome bilayer format was used for the photographic evaluation of the coupler dispersions. The two layers were coated simultaneously over a "gel" pad coated support as illustrated in the diagram below:

| TOP | | |
|---|---|---|
| Layer 2 | Gelatin | 1.614 g/m2 |
| | Alkanol XC | 21.5 mg/m2 |
| | Hardener BVSME * | Added at rate of 1.8% w/w of total gelatin, including "gel" pad |
| | Gelatin | 1.614 g/m2 |
| Layer 1 | Coupler A | 0.836 mmoles/m2 |
| | Silver (as chloride emulsion) | 239.0 mg/m2 |
| "Gel" Pad | Gelatin | 3.229 g/m2 |
| Support///////////// Resin-coated paper ///////////// | | |

\* BVSME: Bis-vinyl-sulphonyl-methyl-ether

The coatings were exposed to white light for 0.1 s through a 21 step 0.15 logE increment tablet and processed in standard RA-4 chemistry. The Dmax density and contrast were measured using an analytical reflection densitometer. Results are shown in Table 3 below.

TABLE 3

Measurements of coated dispersions of Coupler A made with different surfactants.

| SURFACTANT (dispersing aid) | Contrast (±0.06) | Dmax (±0.02) | Comment |
|---|---|---|---|
| X = —CH$_2$C(CH$_3$)$_2$— | 4.90 | 2.79 | invention |
| X = —(CH$_2$)$_3$—, | 4.76 | 2.67 | comparison |
| X = —(CH$_2$)$_2$— | 4.79 | 2.60 | comparison |
| AOT | 4.50 | 2.53 | comparison |
| SDBS | 4.63 | 2.59 | comparison |

Table 3 shows that the dispersing aid of this invention gives improved contrast and Dmax relative to the three types of dispersing aid:

(i) The relative straight chain di-ω-phenylalkyl sulphosuccinates.

(ii) A typical aliphatic sulphosuccinate, such as Aerosol™ OT.

(iii) A typical conventional anionic surfactant, such as SDBS.

We claim:

1. A composition comprising a hydrophilic colloid having hydrophobic particles dispersed therein with the aid of a compound having the structure

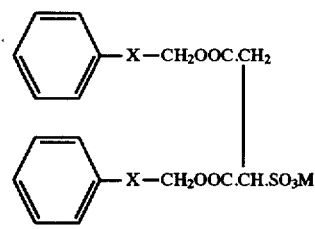

I wherein

M is a cation; and

X represents a group having the structure

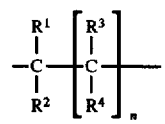

wherein n represents 1;

R¹ and R² are each hydrogen, and R³ and R⁴ are each methyl.

2. A composition according to claim 1 wherein the hydrophilic colloid is gelatin.

3. A composition according to claim 2 wherein the hydrophobic particles comprise a photographic coupler.

4. A composition according to claim 1, wherein the hydrophobic particles comprise a photographic coupler.

5. A multilayer photographic material comprising a support bearing a plurality of hydrophilic colloid layers including at least one light-sensitive silver halide emulsion layer wherein at least one of the underlying layers of the material contains hydrophobic particles dispersed therein with the aid of a compound having the structure

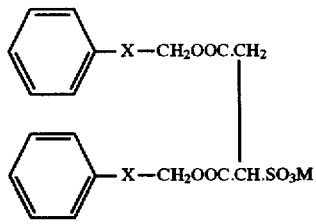

I wherein

M is a cation; and

X represents a group having the structure

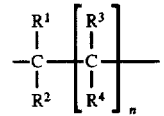

wherein n represents 1;

R¹ and R² are each hydrogen, and R³ and R⁴ are each methyl.

6. A material according to claim 5 wherein the hydrophilic colloid is gelatin.

7. A material according to claim 6 wherein the hydrophobic particles comprise a photographic coupler.

8. A material according to claim 5, wherein the hydrophobic particles comprise a photographic coupler.

* * * * *